(12) United States Patent
Walch

(10) Patent No.: US 6,790,847 B2
(45) Date of Patent: Sep. 14, 2004

(54) TOPICAL APPLICATION OF CETIRIZINE AND LORATADINE

(75) Inventor: Hatto Walch, Baden (DE)

(73) Assignee: Oramon Arzneimittel GmbH, Laupheim (DE)

( * ) Notice: Subject to any disclaimer, the term of this patent is extended or adjusted under 35 U.S.C. 154(b) by 0 days.

(21) Appl. No.: 10/334,331

(22) Filed: Dec. 30, 2002

(65) Prior Publication Data
US 2003/0129209 A1 Jul. 10, 2003

(30) Foreign Application Priority Data
Jan. 4, 2002 (EP) .............................................. 02000131

(51) Int. Cl.$^7$ ........................ A61K 31/50; A61K 31/44; A61K 31/445; A61K 31/74
(52) U.S. Cl. ...................... 514/252; 514/315; 514/279; 424/78.05
(58) Field of Search ............................... 514/252, 315, 514/279

(56) References Cited

U.S. PATENT DOCUMENTS 5,567,420 A  * 10/1996 McEleney et al. ............ 424/60
5,993,833 A    11/1999 De Lacharriere et al.

FOREIGN PATENT DOCUMENTS

| EP | 0 484 529 A1 | 5/1992 |
| EP | 1 005 865 A1 | 6/2000 |
| JP | 62 164624 A | 7/1987 |
| JP | 01 102024 A | 4/1989 |
| JP | 01 121218 A | 5/1989 |
| JP | 09 030972 A | 2/1997 |
| JP | 02 835985 B | 12/1998 |
| WO | WO 92 19276 A | 11/1992 |
| WO | WO 01/39774 A1 | 6/2001 |
| WO | WO 01/87236 A2 | 11/2001 |

OTHER PUBLICATIONS

International Search Report, Appln. No. 02000131.9–2123, dated Jun. 28, 2002.
Origoni et al., "Topical oxatomide: an alternative approach for the treatment of vulvar lichen sclerosus", International Journal of Gynecology and Obstetrics, 1996, pps. 259–264.
Origoni et al., "Efficacy of Topical Oxatomide in Women with Pruritus Vulvae", Drugs. Exptl. Clin. Res., XVI (11), 1990, pps. 591–596.
Sacerdoti et al., "Evalution of the inhibition of allergen–specific and nonspecific skin responses by topical oxatomide," G Ital Dermatol Venereol, vol. 125, No. 7–8, 1990, pps. XXIX–XXXII.
Lodi et al., "Oxatomide in the treatment of pruriginous skin diseases of various nature", G Ital Dermatol Venereol, vol. 125, No. 10, 1990, pps. LV–LIX.
Leggieri et al., "Topical oxatomide in the treatement of urticaria", Reparto di Immunologia e Allergologia Clinica, 1992, pps. 137–144.
Garcia–Campayo et al., "Independent Activities of FSH and LH Structurally Confined in a Single Polypeptide: Selective Modification of the Relative Potencies of the Hormones", Endocrinology, vol. 142(12), 2001, pps. 5203–5211.

* cited by examiner

Primary Examiner—Sreeni Padmanabhan
Assistant Examiner—Jennifer Kim
(74) Attorney, Agent, or Firm—Ratner Prestia

(57) ABSTRACT

The present invention relates to a drug composition containing the non-sedating $H_1$ antihistamines cetirizine, loratadine, mixtures or pharmaceutically acceptable salts thereof for topical application in the form of a gel.

9 Claims, No Drawings

TOPICAL APPLICATION OF CETIRIZINE AND LORATADINE

BACKGROUND OF THE INVENTION

The present invention relates to a pharmaceutical composition comprising the non-sedating $H_1$ antihistamines cetirizine, loratadine, mixtures, or pharmaceutically acceptable salts thereof for topical application in the form of a gel.

Histamine is a biogenic amine formed by decarboxylation of the amino acid histidine and is present as a tissue hormone in human and animal organisms, especially in the skin and in the lung. However, it is also contained in bee poison, in the salivary secretion of biting insects, in stinging nettles, and such like. In the human body, histamine is stored in the basophilic granulocytes and the mastocytes. When allergic skin reactions occur, excess histamine is released and is then one of the factors responsible for itching and the formation of skin weals and flares. This release takes place whenever human and animal cells are damaged and causes reactions of the surrounding tissue. Even though histamine is rapidly metabolised in the human body, the effects caused by the release may last for a considerable period of time which severely affects the well-being of the person concerned. At present, antihistamines are primarily administered orally to treat these effects of histamine releases.

Antihistamines are pharmaceutical agents which competitively displace histamine from its receptors and are therefore able to counteract its effects. Depending on the histamine receptors they effect, they are classified as $H_1$ antihistamines and $H_2$ antihistamines. In addition to their antihistaminic characteristics, almost all $H_1$ antihistamines also have a spasmolytic and locally anaesthetising effect. In addition, most of these preparations have a sedating effect on the central nervous system.

In general, $H_1$ antihistamines are indicated for all diseases based on the release of histamine, substances with a stronger sedating effect also being used as antiemetics or sleeping drugs. In any case, the most important side effect is the influence on the central nervous system, i.e. the sedating effect. Because this sedating effect prevented general application, for example in case of colds or hay fever, second generation $H_1$ antihistamines with fewer sedating side effects have been developed of late. In general and for the purposes of the present application, these are called "non-sedating $H_1$ antihistamines". Typical examples of non-sedating $H_1$-antihistamines are terfenadine, astemizole, antazoline, cetirizine, loratadine, ketotifen, acrivastine, ebastine, efletirizine, epinastine, fexofenadine, levocabastine, mizolastine, oxatomide, sebastine, temelastine and azelastine.

For example, $H_1$ antihistamines are typically administered orally and sometimes nasally in the form of a spray to treat hay fever. Cetirizine or loratadine are preferably used as active ingredients.

According to the American Drugdex Drug Evaluations, cetirizine, a metabolite of hydroxyzine, is a $H_1$ antagonist with non-sedating characteristics. The recommended oral dose for cetirizine is 10 mg once per day for adults or 2.5 to 5 mg once per day for children. In general, cetirizine is used to treat hay fever, allergic rhinitis, chronic urticaria and asthma. Usually, it is administered orally. The intranasal application of a cetirizine spray is also known, even though such formulations are not available commercially.

U.S. Pat. No. 4,525,358 describes the preparation of cetirizine and other hydroxizine derivatives as well as the use as an anti-allergic, anti-histaminic, bronchio-dilatory and anti-spasmodic agent. In a general form, the document also describes a possible oral, parenteral or topical use of the hydroxyzine derivatives disclosed. However, no examples for a topical formulation are given. In case of the above-mentioned indications, cetirizine has, on the whole, been administered only orally or, for experimental purposes, nasally.

Likewise, other second generation $H_1$ antihistamines such as loratadine are exclusively formulated and administered orally in practical applications. According to the American Drugdex Drug Evaluations, loratadine is also a non-sedating anti-histamine. The active ingredient is administered to adults in one oral dose of 10 mg per day and to children in one dose of 5 mg per day. Oral combination products, for example with pseudoephedrine, are also known. Similar to cetirizine, areas of indication for the use of loratadine are allergic rhinitis, asthma and chronic idiopathic urticaria.

The preparation of the substance is described in U.S. Pat. No. 4,282,233, which also describes pharmaceutical preparations for enteral or parenteral administration, but not topical administration of the active ingredient.

European patent application 0 903 151 describes the use of combinations of non-sedating antihistamines and α-adrenergic active ingredients for the topical treatment of rhinitis or conjunctivitis and of symptoms of a cold. The topical preparations described contain the antihistamine in an amount of 0.001% to 0.5%, preferably 0.05% to 0.1%. Apart from that, the application describes only topical formulations for administration via the mucous membranes, namely nose sprays, nose drops or eye drops. Topical application to the skin is not disclosed or intended.

WO 01/87 236 discloses a spray containing a pharmacologically active compound such as an antihistamine to treat insect bites, insect stings, nettle rash, atopical dermatitis and contact dermatitis, as well as sunburn, neurodermatitis, urticaria and eczema. At the same time, the document discloses creams, gels, foams, ointments or lotions containing hydroxyzine. No details concerning these compositions are provided.

U.S. Pat. No. 5,993,833 discloses topical compositions containing an antihistamine, an interleukin-1 antagonist and/or an TNFα antagonist. These preparations may be provided in any topical form possible including anhydrous or lipophilic gels, creams, emulsions, foams and such like. However, this document primarily teaches the addition of an antihistamine to a cosmetic, dermatological or pharmaceutical preparation instead of such as composition per se, the antihistamine not being the actual active ingredient, but merely improving toleration of the latter.

As components of said preparations all customary components such as oils, emulsifiers, solvents (lower alcohols and propylene glycol), hydrophilic gelatinising agents (carbomer, acryl copolymers, polysaccharides such as hydroxy propyl cellulose as well as lipophilic gelatinising agents such as ethyl cellulose and polyethylene) are mentioned. The examples illustrate the use of the antihistamine cetirizine or loratadine as a cream, gel or lotion.

WO 01/39 774 discloses a preparation containing ketotifen which may be used for the treatment of allergic conditions including insect bites and stings, nettle rash, atopical and contact dermatitis as well as eczema, urticaria, neurodermatitis, dry skin and sunburn and may be present in the form of a gel, a lotion, a spray, a foam, a cream, an ointment and different fluids. Even though the preparations may contain various customary components, gels are not especially preferred. Instead, a cream preparation is preferred.

EP 0 484 529 discloses a w/o skin cream preparation comprising an active ingredient such as, among others, ketotifen and a cream base containing a diglycerol fatty acid ester and/or sorbitan fatty acid ester having a HLB of 3 to 7, a polyvalent metallic salt of a fatty acid having 10 to 12 carbon atoms, a salt of an inorganic or organic acid, an oil phase component and water.

The oral administration described above has the disadvantage of a slow onset of the effect. In addition, oral administration is accompanied by the known sedating side effects since the active ingredient is evenly distributed throughout the entire organism. These side effects also occur with second generation $H_1$ antihistamines, albeit in a less severe form. Especially in situations where the person taking it must be fully alert, for example when driving a car, operating complicated machinery etc., sedation constitutes a certain hazard.

Topically, the effects of histamine on the skin are presently treated by applying isoprenaline sulphate, benzocain, diphenhydramine or benzalkonium chloride. Among this group, diphenhydramine is an antihistamine, but has a severe sedating effect. Because of this strong sedating effect, diphenhydramine is also used as a hypnotic agent or as a sedative.

Topical administration of the above-mentioned substances either has the disadvantage that it does not have a sufficiently specific effect on the cause of the disease or disorder, namely the release of histamine, and merely fights the symptoms, for example by numbing the itch. Vice versa, the application of diphenhydramine may have additional sedating side effects, because it is frequently used as a local anaesthetic. In addition, the onset of the effect is comparatively slow.

Also known are the above mentioned topical formulations of ketotifen, cetirizine and loratadine. However, these substances have the disadvantage that the active ingredient does not penetrate the skin easily and the onset of the effect is therefore retarded.

Therefore, it is the object of the invention to provide a fast and locally acting pharmaceutical form of the preferred antihistamines cetirizine and loratadine for the treatment of disorders or diseases of the skin resulting from excessive release of histamine which permits a rapid onset of the effect.

SUMMARY OF THE INVENTION

The present invention relates to a pharmaceutical composition for topical application in the form of a gel, comprising 0.05 to 5 wt. %, preferably 0.5 to 5.0 wt. % of a non-sedating $H_1$ antihistamine selected from the group consisting of cetirizine, loratadine and mixtures and pharmaceutically acceptable salts thereof as well as at least one pharmaceutical carrier or excipient which is a solvent for the antihistamine.

Other advantageous embodiments of the invention are shown in the claims.

DETAILED DESCRIPTION OF THE INVENTION

Surprisingly, it has now been found that the above objects may be achieved and the disadvantages of the prior art overcome by a pharmaceutical composition for topical application in the form of a gel, comprising 0.05 to 5.0 wt.-% of a non-sedating $H_1$ antihistamine selected from the group consisting of cetirizine, loratadine and mixtures and pharmaceutically acceptable salts thereof as well as at least one pharmaceutical carrier or excipient which is a solvent for the antihistamine.

It is one advantage of the topical application of the non-sedating $H_1$ antihistamine cetirizine and/or loratadine in the form of a gel of the invention that the active ingredient counteracts the locally released histamine by binding competitively to the relevant receptor so that symptoms may largely be avoided or reduced. In addition, the formulation of the invention surprisingly produced a faster onset of the effect in comparison with known topical formulations.

Without wishing to be bound by theory, the inventors believe that this may be due to the fact that the active ingredient is not merely suspended in the formulations of the invention, but is present in the form of a genuine solution. In turn, the resulting molecular distribution could increase the speed of resorption.

The gels of the invention are preferably intended for the therapy of a disease or disorder selected from the group consisting of urticaria, allergy-based dermatoses (allergic skin reactions), atopical eczema, itching, redness, sunburn and insect bites.

The gels of the invention permit easy spreading on the skin, especially since these disorders tend to affect large areas, and may have a cooling effect perceived as pleasant by the patient. According to the invention, resorption may be accelerated by formulating the active ingredient in a gel which is easily broken down and therefore releases said active ingredient on the skin more rapidly.

As described above, the pharmaceutical compositions of the invention contain a non-sedating $H_1$ antihistamine selected from the group consisting of cetirizine, loratadine as well as mixtures and pharmaceutically acceptable salts thereof. Such pharmaceutically acceptable salts may be the hydrochloride, hydrobromide, hydroiodide, citrate, carbonate, malate, tartrate etc. Mixtures of cetirizine and loratadine and/or salts thereof may also be used according to the invention.

The gels contain the non-sedating $H_1$ antihistamine and/or a pharmaceutically acceptable salt thereof in an amount of 0.05 to 5.0 wt. %, preferably 0.5 to 5.0 wt. %. More preferably, the formulation contains 0.8 to 1.5 wt.-% of the active ingredient.

In addition, the gels of the invention contain one or more pharmaceutical excipients or carriers. Such pharmaceutical excipients or carriers are preferably selected from pharmaceutical excipients and carriers which are known and suitable for the formulation of the above mentioned composition form. At least one of the excipients and carriers is a solvent for the active ingredient used. As possible pharmaceutical excipients and carriers, mention may be made of solvents such as water, alcohols, especially $C_1$–$C_5$ alcohols such as ethanol, n-propanol, 2-propanol, isopropanol, t-butyl alcohol; ethers such as MTBE; ketones such as acetone, methyl ethyl ketone; humectants such as glycerol; glycols such as ethylene glycol, propylene glycol; emulsifiers such as lower, optionally polyhydric $C_{1-5}$ alcohols partially esterified with long-chain ($C_{12}$–$C_{24}$) fatty acids such as glycerol monostearate, isopropyl myristate, fatty acid ester of sugar alcohols such as sorbitan mono-fatty acid ester, polyethoxylated derivatives of such compounds, polyethoxyethylene fatty acid ester and fatty alcohol ether, cholesterol, cetyl stearyl alcohol, wool wax alcohols and synthetic surfactants with a low HLB value; solubilisers such as carbopol; low-viscosity paraffins, triglycerides; lipophilic substances such as isopropyl myristate; pH regulators such as TEA, carbonates and phosphates; chelating agents such as EDTA and salts thereof; as well as preservatives.

In addition to these pharmaceutical excipients and carriers, the pharmaceutical compositions of the invention may contain one or more cosmetic excipients. Such cosmetic excipients are well known to pharmaceutical formulators. In particular, they may be selected from the group consisting of humectants, smoothing agents, UV filters, pigments, dyes, perfumes, vitamins and bleaching agents. Humectants, smoothing agents and perfumes are especially preferred.

As far as the gels to be used according to the invention are concerned, we must distinguish between hydrophilic gels and hydrophobic gels. In the invention, both may be used, optionally depending on the indication to be treated. As is well known, hydrophilic gels are gels having a high water content (80 to 90%).

The hydrophobic or so-called "oleogels" are greasing gels which are formed with liquid paraffins, polyethylene glycols, triglycerides etc. as the base together with gelatinising agents such as highly dispersed silica or aluminum or zinc soaps. In the invention, hydrophilic gels are particularly well suited for the indications insect bites and sunburn, whereas oleogels are specifically used for atopical eczema.

According to a first embodiment, a gel composition containing 0.05 to 5 wt. %, preferably 0.5 to 5 wt.-%, more preferably 0.8 to 1.5 wt.-% of antihistamine (preferably cetirizine, hydrochloride cetirizine, loratadine hydrochloride, loratadine);

1 to 2 wt.-% of solubiliser, especially carbopol;

0 to 1 wt.-%, especially 0 to 0.4 wt.-% of a chelating agent, especially EDTA;

20 to 40 wt.-%, especially 30 to 40 wt.-%, of alkylene glycol, especially propylene glycol;

5 to 20 wt.-%, preferably 10 to 20 wt.-%, of alcohol, especially n-propanol, isopropanol, 0 to 4 wt.-%, preferably 1 to 4 wt.-%, of pH regulator, especially triethanol amine, and a residual amount of purified water ad 100%, i.e. 20 to 70 wt.-%, preferably 30 to 60 wt.-%, most preferably 35 to 50 wt.-%, the weight ratios of the components adding up to 100% and being based on the overall weight of the composition, is especially preferred.

According to a second preferred embodiment of the invention, a gel is provided containing 0.05 to 5 wt.-%, preferably 0.5 to 5 wt.-%, more preferably 0.8 to 1.5 wt.-% of the active ingredient (preferably cetirizine hydrochloride, cetirizine, loratadine hydrochloride, loratadine);

5 to 20 wt.-%, preferably 10 to 15 wt.-%, of alkylene glycol, especially propylene glycol;

2 to 10 wt.-%, preferably 5 to 10 wt.-%, of ethoxylated partial glycerides of fatty acids, especially medium-chain fatty acids such as the product sold under the trademark Softigen® 767;

3 to 10 wt.-%, preferably 3 to 5 wt.-% of cellulose derivatives, especially cellulose ether such as metholose; and a residual amount of purified water ad 100%, i.e. 50 to 90 wt.-%, preferably 55 to 90 wt.-%, and most preferably 80 to 90 wt.-%, the weight ratios of the above-mentioned substances adding up to 100% and being based on the overall weight of the composition.

According to a third preferred embodiment of the invention, a gel is provided containing 0.05 to 5 wt.-%, preferably 0.5 to 5 wt.-%, more preferably 0.8 to 1.5 wt.-% of the active ingredient (preferably cetirizine hydrochloride, cetirizine, loratadine hydrochloride, loratadine);

1 to 2 wt.-%, preferably 0.6 to 1.0 wt.-% of solubiliser, especially carbopol;

0.2625 to 0.4375 wt.-%, preferably 0.3 to 0.4 wt.-% of an at least 25% aqueous solution of ammonia;

1.5 to 2.5 wt.-%, preferably 1.8 to 2.2 wt.-% of an ester of a $C_{10-20}$ fatty acid with a lower $C_{2-5}$ alcohol, especially isopropyl myristate;

4.5 to 7.5 wt.-%, preferably 5.5 to 6.5 wt.-% of CETIOL V, the generic designation being oleyl oleate;

0.0375 to 0.0625 wt.-%, preferably 0.045 to 0.055 wt.-% of a chelating agent, especially Na-EDTA;

2.25 to 3.75 wt.-%, preferably 2.75 to 3.25 wt.-% of MACROGOL 400 the generic designation being polyethylene glycol;

15.0 to 25.0 wt.-%, preferably 17.0 to 22.0% of a lower secondary $C_{2-5}$ alcohol, especially 2-propanol; and a residual amount of purified water ad 100%, i.e. 47.1625 to 83.9375 wt.-%, preferably 55 to 65 wt.-%, the weight ratios of the above-mentioned substances adding up to 100% and being based on the overall weight of the composition.

The latter gel is a formulation which breaks down especially rapidly on the skin and therefore permits excellent penetration.

The administration form of a gel according to the invention helps avoid the systemic detour and also permits administration of much lower amounts of the active ingredient than required in the past and described as necessary for oral therapy. For example, when 200 mg (approx. 200 µl) of gel with a weight concentration of 0.05 to 5 wt. % of active ingredient are applied, 1 mg of active ingredient is administered.

The invention will now be further illustrated on the basis of the following examples. These are merely used for illustration and are not intended to limit the invention.

EXAMPLES

Example 1

Gel Preparation

A gel preparation was prepared from the following components by a known method:

| | |
|---|---|
| Cetirizine HCl | 1.00 g |
| Carbopol (acrylate) | 1.25 g |
| EDTA | 0.10 g |
| Propylene glycol | 34.00 g |
| n-Propanol | 15.00 g |
| Triethanol amine | 1.67 g |
| Purified water | 45.98 g |
| | 100.00 g |

The gel preparation of example 1 was tested on 20 volunteers suffering from itching after insect bites or sunburn. It was shown that both the sunburn and the itching and redness disappeared quickly. In addition, the gel was well tolerated by the skin.

Example 2
Gel Preparation

A gel preparation was prepared from the following components by a conventional method:

| | |
|---|---:|
| Cetirizine HCl | 1.00 g |
| Propylene glycol | 10.00 g |
| Softigen ® 767 | 5.00 g |
| Metolose | 3.00 g |
| Purified water | 81.00 g |
| | 100.00 g |

Example 3
Gel Preparation

A gel preparation was prepared from the following components by a conventional method:

| | |
|---|---:|
| Loratadine HCl | 1.000 g |
| Carbopol | 0.800 g |
| 25% solution of ammonia | 0.350 g |
| Isopropyl myristate | 2.000 g |
| CETIOL V | 6.000 g |
| Liquid paraffin | 2.000 g |
| Na-EDTA | 0.050 g |
| MACROGOL 400 | 3.000 g |
| 2-Propanol | 20.000 g |
| Purified water | 65.550 g |
| | 100.000 g |

What is claimed:

1. A drug composition for topical application in the form of a gel, comprising
   0.05 to 5.0 wt.-% of a non-sedating $H_1$ antihistamine selected from the group consisting of cetirizine, loratadine and mixtures thereof;
   1.0 to 2.0 wt.-% of carbopol;
   0 to 0.4 wt.-% of EDTA;
   20 to 40 wt.-% of n-propanol;
   10 to 20 wt.-% of triethanol amino; and
   water ad 100%.

2. A drug composition for topical application in the form of a gel comprising
   0.05 to 5.0 wt.-% of a non-sedating $H_1$ antihistamine selected from the group consisting of cetirizine, loratadine and mixtures thereof;
   5 to 20 wt.-% of propylene glycol;
   2 to 10 wt.-% of an ethoxylated partial glyceryde of medium-chained fatty acids;
   3 to 10 wt.-% of cellulose ether; and
   water ad 100%.

3. A drug composition for topical application in the form of a gel comprising
   0.05 to 5.0 wt.-% of the a non-sedating $H_1$ antihistamine selected from the group consisting of cetirizine, loratadine and mixtures thereof;
   0.6 to 1.0 wt.-% of carbopol;
   0.2625 to 0.4375 wt.-% of an at least 25% aqueous solution of ammonia;
   1.5 to 2.5 wt.-% of isopropyl myristate;
   4.5 to 7.5 wt.-% of CETIOL V oleyl oleate;
   0.0375 to 0.0625 wt.-% of sodium EDTA;
   2.25 to 3.75 wt.-% of MACROGOL 400 polyethylene glycol;
   15.0 to 25.0 wt.-% of 2-propanol; and
   water ad 100%.

4. A drug composition for the treatment of a disease or disorder selected from the group consisting of urticaria, allergy-based dermatoses, atopical eczema, itching, redness, sunburn and insect bites comprising
   0.05 to 5.0 wt.-% of a non-sedating $H_1$ antihistamine selected from the group consisting of cetirizine, loratadine and mixtures thereof;
   1.0 to 2.0 wt. % carbopol;
   0 to 0.4 wt. % of EDTA
   20 to 40 wt. % of n-propanol
   10 to 20 wt. % of triethanol amino; and
   water ad 100%.

5. A drug composition according to claim 4 also comprising one or more cosmetic adjuvants.

6. A drug composition for the treatment of a disease or disorder selected from the group consisting of urticaria, allergy-based dermatoses, atopical eczema, itching, redness, sunburn and insect bites comprising:
   0.05 to 5.0 wt.-% of a non-sedating $H_1$ antihistamine selected from the group consisting of cetirizine, loratadine and mixtures thereof;
   5 to 20 wt.-% of propylene glycol;
   2 to 10 wt.-% of an ethoxylated partial glyceryde of medium-chained fatty acids;
   3 to 10 wt.-% of cellulose ether; and
   water ad 100%.

7. A drug composition according to claim 6 also comprising one or more cosmetic adjuvants.

8. A drug composition for the treatment of a disease or disorder selected from the group consisting of urticaria, allergy-based dermatoses, atopical eczema, itching, redness, sunburn and insect bites comprising:
   0.05 to 5.0 wt.-% of a non-sedating $H_1$ antihistamine selected from the group consisting of cetirizine, loratadine and mixtures thereof;
   0.6 to 1.0 wt.-% of carbopol;
   0.2625 to 0.4375 wt.-% of an at least 25% aqueous solution of ammonia;
   1.5 to 2.5 wt.-% of isopropyl myristate;
   4.5 to 7.5 wt.-% of CETIOL V oleyl oleate;
   0.0375 to 0.0625 wt.-% of sodium EDTA;
   2.25 to 3.75 wt.-% of MACROGOL 400 polyethylene glycol;
   15.0 to 25.0 wt.-% of 2-propanol; and
   water ad 100%.

9. A drug composition according to claim 8 also comprising one or more cosmetic adjuvants.

* * * * *